United States Patent

Zine, Jr.

[11] 4,046,699
[45] Sept. 6, 1977

[54] ACCESS DEVICE FOR CENTRIFUGAL SEPARATION ASSEMBLIES

[75] Inventor: Anthony R. Zine, Jr., Corning, N.Y.

[73] Assignee: Corning Glass Works, Corning, N.Y.

[21] Appl. No.: 737,536

[22] Filed: Nov. 1, 1976

[51] Int. Cl.² .............................................. B01D 21/26
[52] U.S. Cl. .............................. 210/516; 210/DIG. 23
[58] Field of Search ................ 23/230 B, 258.5, 259, 23/292; 128/2 F, 214 R, 218 M, 272.1, DIG. 5; 210/83, 84, 359, 514–518, DIG. 23, DIG. 24; 233/1 R, 26

[56] References Cited

U.S. PATENT DOCUMENTS

| 982,328 | 1/1911 | Wheeler | 210/516 |
|---|---|---|---|
| 3,355,098 | 11/1967 | Farr | 210/DIG. 23 |
| 3,512,940 | 5/1970 | Shapiro | 210/359 X |
| 3,661,265 | 5/1972 | Greenspan | 210/359 |
| 3,865,731 | 2/1975 | Seitz | 210/359 |
| 3,905,528 | 9/1975 | Maiocco | 233/26 |
| 3,920,549 | 11/1975 | Gigliello et al. | 210/83 |
| 3,962,085 | 6/1976 | Liston et al. | 210/359 X |
| 3,981,804 | 9/1976 | Gigliello | 210/DIG. 23 |

Primary Examiner—Wilbur L. Bascomb, Jr.
Assistant Examiner—Robert H. Spitzer
Attorney, Agent, or Firm—Burton R. Turner; Clarence R. Patty, Jr.

[57] ABSTRACT

In apparatus for effecting a sealed separation or partition between two phases of a multiphase liquid upon centrifugation of the multiphase liquid, a device which facilitates access through the partition to a phase of a separated multiphase liquid which is confined between the partition and a lower or closed end of a vessel retaining such liquid.

10 Claims, 5 Drawing Figures

ACCESS DEVICE FOR CENTRIFUGAL SEPARATION ASSEMBLIES

BACKGROUND OF THE INVENTION

In U.S. Pat. No. 3,852,194, issued to me on Dec. 3, 1974, an apparatus for fluid collection and partitioning is shown as including an evacuated container or vessel having a closed end with gel-like material positioned therein and an open end sealed by a needle-puncturable stopper. A fluid having differing density phases such as blood is siphoned into the vessel through the stopper, and centrifugation is applied to the vessel to separate the fluid into at least two phases. The gel-like material is preferably thixotropic and has a specific gravity or density which is intermediate the densities of the two phases to be separated and accordingly moves during centrifugation to an interface position between the phases. After centrifugation, the material is adapted to form a physical and chemical seal or partition with the vessel sidewalls between the separated phases, which permits the light phase of the multiphase fluid to be simply decanted from above the material.

Such apparatus and method permits blood to be collected, centrifuged, and physically partitioned without removal of the stopper. It will be appreciated that this closed method is of great advantage to hospital or laboratory personnel, not only due to its convenience but also to its inherent protection against infections from contact with contents of the separation vessel. However, the gel-like partitioning material restricts access to the heavy red cell phase between it and the bottom end of the tube.

A main feature of the present invention is the provision of an access device which may be used in a partially evacuated collection and separation apparatus to provide, after centrifugation, access through the partitioning material to at least a sample quantity of the separated heavy phase below the partitioning material.

Although the heavy phase access device of the present invention has particular use in the closed collection and separation devices generally described above, it is also useful in centrifugal separation systems wherein the partitioning material is added to the separation container after collection of the multiphase fluid. Further, it may be used in systems which utilize any kind of inert barrier fluid or semi-fluid of a selected density to form a fluid or semi-fluid barrier between phases of a specimen fluid upon centrifugation of the specimen fluid into its phases. For example, the access device could be used in a silicone oil flotation method of fractionating cellular matter from body fluids. In such a method, which is believed to have been first described by S. H. Seal in Cancer (1959, 12:590–595), a blend of silicone oils is used in an "open" sequence to form a fluid barrier between two phases. The access device of the present invention may be used to provide access to, and removal of, the heavy phase below the fluid barrier. The device is also useful in a beads-plus-adhesive separator assembly, such as described in U.S. Pat. No. 3,920,557, wherein a mixture of adhesive and beads is distributed from an upper end of the centrifugation vessel.

SUMMARY OF THE INVENTION

In accomplishing the foregoing objects, the present invention provides a heavy phase access device or accessor comprising a first portion embodying support or base means for supporting an upright second portion and for directing the flow of partitioning fluid upwardly along sidewall portions of a centrifugation vessel; and a second portion embodying upright tubular means, connected to and supported by said base means, for providing an access to the separated heavy phase of a fluid. In a preferred embodiment, the base means or flow control portion is test tube shaped and the tubular means or access portion includes a tube, connected to the base means by struts, which tube extends coaxially from the upper open end of the test tube shaped flow control portion to a selected distance thereabove.

The access device may be employed in combination with a closed, evacuated multiple phase fluid collection and centrifugal separation assembly including a vessel, a quantity of highly viscous preferably thixotropic partitioning material at one closed end of the vessel, and a needle-pierceable stopper within an open end of the vessel. The base means or flow control portion of the access device is initially partially submerged within the partitioning material, and during handling prior to centrifugation, the device is retained within the partitioning material, thus preventing its movement toward the stopper. During centrifugation, the flow control portion initiates and directs the flow of the partitioning material through peripheral portions of the blood. Upon the termination of the centrifugal force, the partitioning material lies wholly outside the tubular access portion, effectively sealing the light and heavy phases surrounding the access portion but not the phases within such tubular portion itself.

Preferably the tubular access portion has an air-permeable and pierceable membrane at its uppermost end which is adapted to permit air to escape from the access portion during filling and centrifuging. The membrane also prevents the contents of the tube from being poured out of the access portion during the decanting or removal of the light phase from the vessel, and is of a material which may be penetrated by a pipet or syringe tip for removal of a sample of the heavy phase in the lower portion of the vessel, either before or after removal of the light phase.

The access device may also be utilized in providing access to a heavy phase of a fluid in a system which uses a non-thixotropic partitioning fluid, such as a grease or a blend of fluids. This type of system comprises a container and a partitioning fluid initially deposited at a closed end thereof. The multiphase fluid to be separated is layered over the partitioning fluid, and due to the selected specific gravity of partitioning fluid, it flows during centrifugation to an interface position between separated phases of the multiphase fluid. The access device is preferably first partially submerged in the partitioning fluid and the multiphase fluid is thereafter supplied to the vessel. After centrifugation, the light phase above the partitioning fluid is removed by aspiration, and the heavy phase below the partitioning fluid can be partially removed by aspiration or pipetting through the access portion of the device.

DESCRIPTION OF THE PREFERRED EMBODIMENTS

Figure 1:
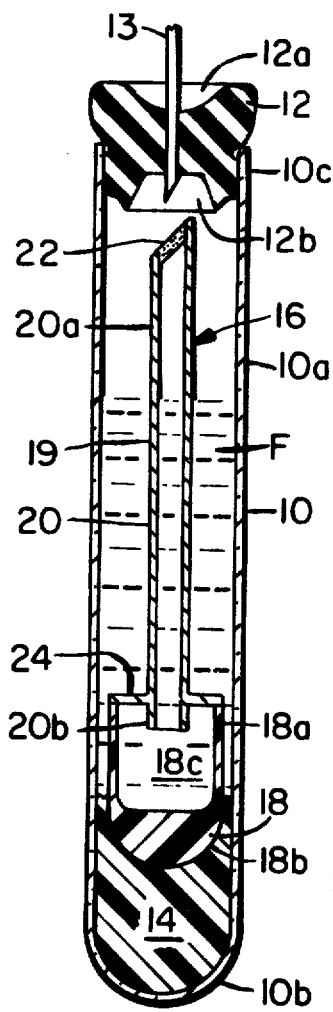
FIG. 1 is an elevational cross-sectional view showing the access device of the present invention in combination with an evacuated blood collection, separation, and partitioning assembly; this view illustrates the operational step of siphoning blood into the assembly through a needle which has penetrated the stopper of the assembly.
Figure 2:
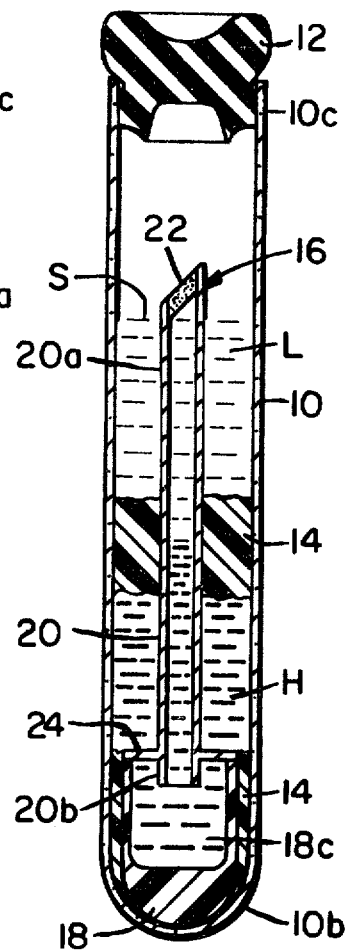
FIG. 2 is a view similar to that of FIG. 1 but illustrates the relative positions of the blood phases, the partitioning material, and the access device immediately after centrifugation.
Figure 3:
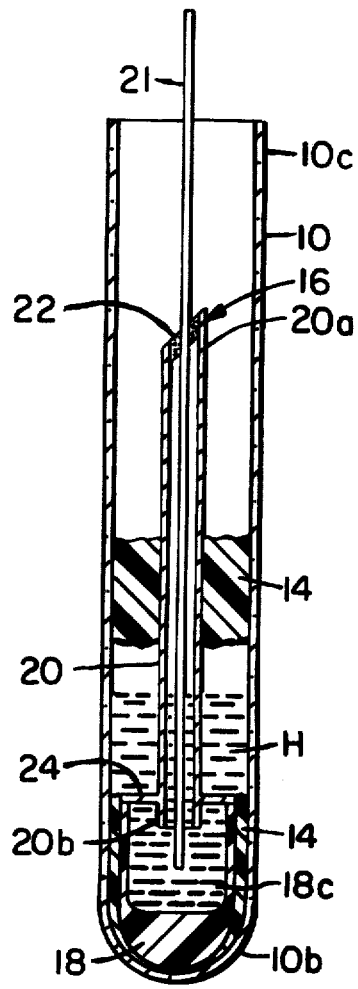
FIG. 3 is similar to both FIGS. 1 and 2, but depicts the method of removing the heavy phase of the blood from within the access device by means of a pipet; in this view, the light phase has already been removed, such as by decanting.

As shown in FIGS. 1-3, the present invention is described in connection with a collection, separation and partitioning apparatus which remains closed to the ambience from collection through separation and partitioning. The basic apparatus includes a container or vessel 10 having a cylindrical sidewall 10a which is closed at one end 10b and open at its other end 10c. The open upper end 10c is sealed with a stopper 12 which forms an air-tight seal with the vessel to thus provide a vessel which may be partially evacuated. The stopper 12 is made from an elastomeric material, such as natural rubber, and preferably includes depressions 12a and 12b on its upper and lower surfaces which form an easily penetratable self-sealing membrane therebetween. The membrane may be easily penetrated by a double ended needle or cannula 13 during the siphoning of a multiphase fluid F, such as blood, into the vessel.

When used in the standard manner to siphon blood from a patient, a selected quantity of a partitioning material 14 is deposited at the lower closed end 10b of the vessel 10. The partitioning material 14 is preferably a thixotropic fluid, such as a silicone fluid, so that the fluid is substantially non-flowable at rest but flows during centrifugation. When thixotropic, the fluid has an initially high viscosity which becomes less viscous during centrifugation and which, after termination of centrifugation reverts back to a high viscosity. Although the present invention is not limited for use in combination with thixotropic partitioning materials, in a closed system, a highly viscous partitioning fluid functions to initially retain the extraction device in position and prevent it from moving toward the stopper when the vessel assembly is being used to siphon blood. However, since thixotropic fluids are highly viscous at rest and during normal handling, but thin out and readily flow during centrifugation, thixotropic materials are deemed to be the best form of partitioning material for use with the access device of this invention.

The access or extraction device 16 comprises a base or flow control portion 18 and an interconnected tubular access portion 19. The access device 16 should have a composite density or specific gravity greater than that of the heavy phase of the multiphase fluid F to be separated, and preferably greater than that of the multiphase fluid F so that it will rapidly move toward the bottom end 10b of the vessel during centrifugation. The device 16 may be made from any material which is non-interactive with the multiphase fluid, its components or any chemical additives to the vessel, such as an acrylic plastic, subject to the aforenoted density requirement.

The flow control portion 18 may be identical with the flow control members or energizer means shown and described in either U.S. Pat. No. 3,920,549 to Gigliello et al. or U.S. Pat. No. 3,981,804 to J. Gigliello. Reference is directed thereto and the contents thereof are incorporated hereinto to the extent of explaining the operation of flow control members used with thixotropic or gel-like partitioning materials. However, the flow control portion 18 of the device 16 need not include the construction details of the foregoing patents, as the device 16 is equally useful in systems not having a thixotropic partitioning material and in open systems wherein the accessor 16 is placed into an open vessel either before supplying multiphase fluid to the vessel or after such supply, but before centrifugation.

Referring again to the "closed" system as shown in FIGS. 1-3, the support base or flow control portion 18 is shown in the configuration of a test tube having a rounded bottom end 18b and a cylindrical sidewall extending from an upper diameter of the bottom end 18b and terminating in an upper end 18a which is shown lying in a plane normal to the axis of the cylindrical sidewall. A cavity 18c, formed in the upper end 18a, extends downwardly into the flow control portion 18. The cavity 18c may have a cylindrical contour or a downwardly and inwardly tapering contour.

Figure 4:
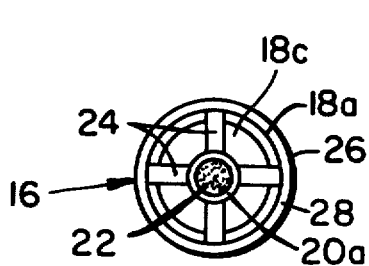
FIG. 4 is a top plan view of a preferred embodiment of the access device.

The access portion 19 of the extraction device 16 includes a cylindrical tubular section 20 having a top end 20a and a bottom end 20b. The access portion may be connected to the upper end 18a of the flow control portion by a plurality of struts 24 which extend radially outwardly from the tubular section 20 and lie in a plane normal to the axis of the cylindrical section. In the embodiment of FIGS. 1-3, the struts 24 have the same top plan configuration as shown in FIG. 4 for another embodiment hereinafter discussed. That is, four struts angularly displaced by quadrants about the tubular section 20 may be formed integrally with the tubular section. Each of the struts are shown of equal length with the outer ends thereof connected to portions of the upper end 18a of the flow control portion 18 such as by an adhesive, sonic welding, or other means of attaching the two parts. The access portion as shown is thus interconnected by the struts in a coaxial upwardly extending relationship to the flow control portion, such that the tube 20 is coaxial with the longitudinal axis of the flow control portion 18.

As will be appreciated by those skilled in the centrifugal separation art, especially in the blood separation field thereof, it is desirable that the fluid to be separated be permitted as much freedom of flow as possible. Conversely, it is important to reduce the disturbance or agitation of the fluid during centrifugation which may be caused by the access device. Accordingly, the access or extraction device 16 preferably, but not necessarily, has a shape which is symmetrical about a line or axis; more specifically, all surfaces of the device may be surfaces of revolution about the axis of the device, except for the surfaces of the support struts 24 which are symmetrical about the axis. Such symmetry may help facilitate the axis of the device aligning itself with an orientation virtually coaxial with the axis of the vessel 10 during centrifugation and retaining such aligned orientation while the device is forced toward the tube bottom end 10b into the partitioning material 14.

As centrifugation continues, the phases of the multiphase fluid will separate, the heavy phase being caused to flow toward the tube bottom 10b, and the light phase being caused to flow in the direction of the open end 10c and layer over the heavy phase. The partitioning material 14 is caused to flow to an interface position between the phases due to its intermediate density, thus separating the phases upon completion of centrifugation and forming a barrier or partition between the separated phases as shown in FIG. 2. As noted, the barrier 14 forms a seal between the outer wall of tube 20 and the inner wall of vessel 10.

The partitioning material 14 is directed, by the flow control portion 18 during centrifugation, through peripheral portions of the multiphase fluid upwardly along the portions of the sidewall 10a of the vessel, and due to the radially-inward spacing of the tubular section 20 and particularly the lower end 20b, relative to the cylindrical sidewall of the base 18, the partitioning material 14 will not enter the access tube 20. Rather, as shown in FIG. 2, the material 14 forms a seal with outer surface portions of the tubular section 20 and radially aligned or registered inner surface portions of the container sidewall 10a which are in contact with the material 14. Thus, the seal or partition material 14 is wholly outside of the tubular section 20. On the interior of the tubular section, the separated phases are adjacent each other with the light phase being layered over the heavy phase, as in prior art devices conventionally used before the advent of the aforenoted partitioning devices.

The separated and partitioned assembly existing after centrifugation permits the light phase L, which is outside the tubular section 20 and above the partitioning material 14, to be temporarily stored without concern for its contamination by the heavy phase H. However, since there is no partitioning material within the tubular section 20, the small volume of the contents within such section are retained in a similar manner to that which would be obtained in a centrifugation vessel not having any partitioning material 14 therein. To obtain access to the heavy phase, as shown in FIG. 3, a pipet may be inserted into the axially aligned tube 20 through the light phase and into the heavy phase. Alternatively the light phase within the device may be first aspirated to permit unobstructed access to the heavy phase.

As briefly noted above, the highly viscous partitioning material tends to retain the accessor 16 in position, which is of great importance during the siphoning of blood into the vessel 10, wherein the closured end 10c is normally positioned downwardly during the siphoning step. This retention feature which is obtained by the flow control portion 18 initially protruding into material 14, is very beneficial in the blood collection and separation practice because should the siphoning or drawing of blood be spoiled, another draw would be necessary, with the painful and wasteful consequences of the second draw being obvious. Moreover, the retention of the accessor or extraction device 16 by the partitioning material 14, permits a simple construction wherein the upstanding tube 20 requires no transversely extending support or spacer members at its upper end for maintaining the tube at a distance from the stopper cavity. Such a transverse structure, if it were necessary, could inhibit access to the light phase after separation, such as during an automatic light phase removal, and it could also retain cellular material during centrifugation which would hence contaminate the light phase during pour-off or decanting of the light phase. Also, such a transverse structure could tend to cause downwardly moving cellular matter to become ruptured or lysed, as the matter would impinge on such a structure.

Figure 5:
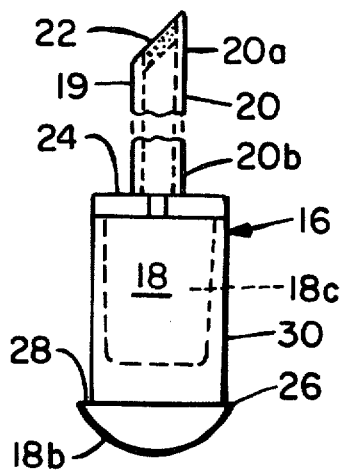
FIG. 5 is an elevational view of the access device shown in FIG. 4.

In actual testing, a separation assembly was provided with a thixotropic partitioning material comprising a mixture of a silicone oil and a siliceous particulate filler and an accessor of the construction shown in FIGS. 4 and 5 was partially submerged in the material. The assembly was evacuated and stoppered. In the siphoning of blood into the assembly from a person, the stoppered end of the vessel was downwardly inclined in the process of piercing a vein with a double-ended needle, with the stopper receiving the other end of the needle. Due to the retention of the accessor 16 by the partitioning material 14, the tube 20 of the accessor remained clear of the bottom cavity 12b of the stopper, thus precluding the possibility that the needle end piercing the stopper would become obstructed by the access tube 20.

The partitioning material 14 is preferably highly viscous to also maintain the accessor or extraction device 16 in a sealed relationship within the material 14 during handling after separation. However, if care is taken, the material 14 may be a fluid having Newtonian flow characteristics and a relatively low viscosity.

When the accessor is used with a partitioning material which is viscous enough in its sealing position to allow the light phase to be decanted, the access tube 20 is preferably provided with a pierceable gas-permeable membrane 22 at its upper end. The membrane 22, which may be formed of an inert open cellular foam plastic or porous paper, prevents the contents of the tube 20 from flowing out of the tube during the decanting of the vessel 10, and hence prevents the possibility of contamination of the light phase L with the heavy phase H contents within and below the access tube 20. During the filling of the vessel 10, the permeability of the membrane 22 allows any air within the tube 20 to escape as the multiphase fluid F fills the tube through its bottom end 20b. Such venting of the tube assures that the composite specific gravity of the access device 16 will not be reduced by gases in the tube 20.

After centrifugation and removal of the light phase from above the barrier of partitioning material 14, depending on whether the heavy and light phases within the tube are interactive with each other, the vessel 10 may be resealed with stopper 12 and the contents stored. However, when blood is the multiphase fluid, it is not possible to store the light phase of serum or plasma for very long above the heavy cellular phase, because the phases are interactive within tube 20. In any event, when it is desired to remove some heavy phase matter as shown in FIG. 3, a pipet or syringe 21 is used to pierce the membrane 22 and extend downwardly through hollow tube 20 to withdraw a sample of the desired phase. For example, a Pasteur pipet or a capillary may be used to extract red cells which may be used for cold agglutination tests in serology. In blood-banking, the cells would be used for ABO, RH and compatability testing.

Referring now to FIGS. 4 and 5, a further embodiment of the access or extraction device 16 is shown having a base or flow control portion 18 and an interconnected tubular access portion 19. The device is similar to that shown in FIGS. 1-3, with the exception that the flow control portion 18 has an upright cylindrical sidewall 30 which is radially inwardly offset by a ledge or recess 28 from the upper outermost peripheral edge 26 of the rounded bottom end 18b. The offset from the edge 26 produced by the recess or ledge 28 inhibits the flow of the partitioning material 14 by capillary action upwardly along the sidewalls of the control portion 18, by providing an increase space between the sidewalls 30 of the control portion 18 and the inner walls of the vessel 10. As shown, the cavity 18c formed within the flow control portion 18 may have tapered sidewalls.

The access portion 19 may be mounted on or connected to the base or support means 18 through use of radially disposed struts 24, as more particularly shown in FIG. 4. The height of the tubular section 20, in both the embodiments shown in FIGS. 1–3 and FIGS. 4 and 5, should be such so that the upper end 20a, containing the porous membrane 22, is above the surface S of the lighter phase L after centrifugation, as shown in FIG. 2. Although only the lighter phase will be present within the upper end 20a of the tube 20 after centrifugation, should the membrane 22 be below the surface S, the lighter phase L within the vessel 10 above the partitioning material 14 could possibly become contaminated by the heavier phase H, if it were stored for any length of time, due to the interaction which might take place within the tube 20 between the unpartitioned interface of the lighter phase L and heavier phase H contained therewithin.

Modifications or variations of the access device will be realized by those skilled in the centrifugal separation art. It is understood that the access device need not have a cylindrical access tube, but may instead have an access tube contour suited for the pipetting or fluid handling device to be used. Also, the flow control portion and structure for connecting the access tube to the flow control portion may be constructed in forms other than shown herein. As previously emphasized, the access device is applicable for use in a separator system which utilizes a partitioning material which is neither thixotropic nor highly viscous. It will be also recognized that the multiple phase fluid to be separated is not limited to a combination of two liquids of differing densities, but may include combinations of solids, cellular matter and liquids which are capable of centrifugal separation in a vessel.

Accordingly, it is to be understood, especially by those skilled in the art, that the present invention may take forms other than those illustrated and described herein, and changes in details may be made without departing from the principles of the invention as set forth in the following claims.

I claim:

1. An access device for use in combination with a multiple phase fluid having a light phase and a heavy phase for gaining access to the separated heavy phase of the multiple phase fluid comprising, upright tubular means for providing access to the separated heavy phase of a multiphase fluid, and base means for supporting said upright tubular means, said base means having a closed bottom end and an open upper end, said open upper end having a cavity formed therein extending downwardly within said base means, means for mounting said upright tubular means on an upper portion of said base means, said tubular means including a tubular portion extending upwardly from said base means and having a top end and a bottom end, said bottom end being positioned in open communication with said cavity formed in said base means for access to a separated heavy phase, said top end being provided with a porous membrane, and said access device having an apparent specific gravity greater than the specific gravity of the heavy phase of said multiple phase fluid.

2. An access device as defined in claim 1 wherein said upright tubular means and said base means are symmetrical about a common longitudinal access.

3. An access device as defined in claim 1 wherein said base means has cylindrical sidewall portions, and said mounting means for said tubular means includes spaced members which maintain said cavity in the upper end of said base means open to the exterior thereof.

4. An access device as defined in claim 3 wherein said cylindrical sidewalls are recessed from the outermost periphery of said closed bottom end.

5. In combination with a vessel for collecting and partitioning multiphase fluids into an upper light phase and a lower heavy phase, an access device having an apparent specific gravity greater than the specific gravity of the heavy phase to be separated for permitting access to and extraction of such lower separated heavy phase of the multiphase fluid comprising, vessel means for collecting and partitioning a multiphase fluid into a light phase and a heavy phase and for receiving said access device, partitioning media in said vessel for partitioning separated light and heavy phases of the multiphase fluid, said access device including upright tubular means for providing access to the separated heavy phase of a multiphase fluid, and base means for supporting said upright tubular means and for directing the flow of said partitioning media for partitioning separated light and heavy phases of the multiphase fluid, said upright tubular means including a tubular section having an upper end adapted to extend above the upper surface of a separated light phase and an open lower end adapted to be an open communication with a separated heavy phase, said tubular section having an outer surface which is radially inwardly offset from the outer periphery of said base means, and means for mounting said upright tubular means on an upper portion of said base means.

6. The combination as defined in claim 5 wherein said partitioning media is initially positioned adjacent a lower end of said vessel, and said base means is partially submerged in said media for initially retaining said access device in such position within said vessel.

7. The combination as defined in claim 5 wherein said upright tubular means and said base means are substantially symmetrical about a common longitudinal access.

8. The combination as defined in claim 5 wherein said base means has an upwardly open cavity formed in an upper surface thereof, and the lower end of said tubular section is in open communication with said cavity.

9. The combination as defined in claim 5 wherein the upper end of said tubular section is provided with a porous membrane.

10. The combination as defined in claim 5 wherein said tubular means upon separation and partitioning of said multiphase fluid into an upper lighter phase and a lower heavier phase, projects through said partitioning media with such media forming a seal with an outer portion of said tubular section intermediate its ends and an inner surface of said vessel, and said open lower end being in communication with said heavy phase while said upper end extends above an upper surface of said lighter phase.

* * * * *